(12) United States Patent
Yamamoto

(10) Patent No.: US 9,169,480 B2
(45) Date of Patent: Oct. 27, 2015

(54) METHOD FOR PREPARING PROTEIN, DNA, AND RNA FROM CELL

(75) Inventor: Nobuko Yamamoto, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 50 days.

(21) Appl. No.: 13/318,337

(22) PCT Filed: May 26, 2010

(86) PCT No.: PCT/JP2010/059293
§ 371 (c)(1),
(2), (4) Date: Oct. 31, 2011

(87) PCT Pub. No.: WO2010/140598
PCT Pub. Date: Dec. 9, 2010

(65) Prior Publication Data
US 2012/0053329 A1    Mar. 1, 2012

(30) Foreign Application Priority Data

Jun. 2, 2009  (JP) ................................. 2009-132911

(51) Int. Cl.
*C12Q 1/00* (2006.01)
*C12Q 1/08* (2006.01)
*C12N 5/00* (2006.01)
*C12N 9/00* (2006.01)
*C12N 15/10* (2006.01)
*C07K 1/34* (2006.01)

(52) U.S. Cl.
CPC .............. *C12N 15/1017* (2013.01); *C07K 1/34* (2013.01)

(58) Field of Classification Search
CPC .......... C12Q 1/24; C12Q 1/68; C12Q 1/6802; C12Q 1/6806; C12Q 1/6811; G01N 33/00; G01N 33/483; G01N 33/487; G01N 15/00; G01N 2015/0019; G01N 2030/0075; G01N 2030/009
See application file for complete search history.

(56) References Cited

U.S. PATENT DOCUMENTS

| 5,004,806 A | 4/1991 | Kung |
| 5,227,470 A | 7/1993 | Kanno et al. |
| 5,352,609 A | 10/1994 | Boquet |
| 5,374,715 A | 12/1994 | Kanno et al. |
| 5,447,864 A | 9/1995 | Raybuck et al. |

(Continued)

FOREIGN PATENT DOCUMENTS

| EP | 0 587 951 A1 | 3/1994 |
| JP | 6-500931 A | 2/1994 |

(Continued)

OTHER PUBLICATIONS

PCT International Search Report and Written Opinion of the International Searching Authority, International Application No. PCT/JP2010/059293 Mailing Date May 26, 2010.

(Continued)

*Primary Examiner* — Ja'Na Hines
(74) *Attorney, Agent, or Firm* — Fitzpatrick, Cella, Harper and Scinto

(57) ABSTRACT

An object of the present invention is to prepare DNA, RNA, and a protein from one cell and to provide a convenient preparation method with high reproducibility. To prepare a protein, DNA, and RNA from a cell, nuclear and cytoplasmic separation is performed, and a protein, DNA, and RNA are then extracted.

12 Claims, 8 Drawing Sheets

(56) References Cited

U.S. PATENT DOCUMENTS

| | | |
|---|---|---|
| 5,545,521 A | 8/1996 | Okamoto et al. |
| 5,624,798 A | 4/1997 | Yamamoto et al. |
| 5,670,315 A | 9/1997 | Yamamoto et al. |
| 5,705,346 A | 1/1998 | Okamoto et al. |
| 5,830,643 A | 11/1998 | Yamamoto et al. |
| 5,939,256 A | 8/1999 | Yamamoto et al. |
| 6,022,961 A | 2/2000 | Yamamoto et al. |
| 6,156,506 A | 12/2000 | Yamamoto et al. |
| 6,297,008 B1 | 10/2001 | Okamoto et al. |
| 6,569,671 B1 | 5/2003 | Okamoto et al. |
| 6,718,742 B1 | 4/2004 | Baker |
| 6,737,238 B2 | 5/2004 | Suzuki et al. |
| 6,844,158 B1 | 1/2005 | Mitsuhashi |
| 6,852,851 B1 | 2/2005 | Tooke et al. |
| 6,960,432 B2 | 11/2005 | Okamoto et al. |
| 6,963,397 B2 | 11/2005 | Suzuki et al. |
| 7,273,697 B2 | 9/2007 | Yamamoto et al. |
| 7,402,384 B2 | 7/2008 | Okamoto et al. |
| 7,445,899 B2 | 11/2008 | Yamamoto et al. |
| 8,080,381 B2 | 12/2011 | Yamamoto et al. |
| 2003/0152998 A1* | 8/2003 | Mitsuhashi ............ 435/6 |
| 2004/0072193 A1* | 4/2004 | Mitsuhashi ............ 435/6 |
| 2004/0224344 A1* | 11/2004 | Han et al. ............ 435/6 |
| 2004/0259221 A1 | 12/2004 | Zhao |
| 2006/0228711 A1 | 10/2006 | Yamamoto |
| 2007/0264635 A1 | 11/2007 | Suzuki et al. |
| 2008/0051293 A1 | 2/2008 | Yamamoto et al. |
| 2009/0011413 A1 | 1/2009 | Ishii et al. |

FOREIGN PATENT DOCUMENTS

| | | | |
|---|---|---|---|
| JP | 6-205676 A | 7/1994 | |
| JP | 6-315374 A | 11/1994 | |
| JP | 8-280384 A | 10/1996 | |
| JP | 9-187277 A | 7/1997 | |
| JP | 2001-506005 A | 5/2001 | |
| JP | 2002-505080 A | 2/2002 | |
| JP | 2002-69095 A | 3/2002 | |
| JP | 2003-144149 A | 5/2003 | |
| JP | 2003-516125 A | 5/2003 | |
| JP | 2004-519234 * | 7/2004 | ............ C12N 15/10 |
| JP | 2004-519234 A | 7/2004 | |
| JP | 2006-51042 A | 2/2006 | |
| WO | 98/26284 A1 | 6/1998 | |
| WO | 99/32654 A1 | 7/1999 | |
| WO | 02/066637 A2 | 8/2002 | |
| WO | 03/035895 A2 | 5/2003 | |
| WO | 03/086273 A2 | 10/2003 | |
| WO | 2009/070558 A1 | 6/2009 | |

OTHER PUBLICATIONS

European Search Report dated May 16, 2013 in European Application No. 10783380.8.

Leadon, et al., "A Rapid and Mild Procedure for the Isolation of DNA from Mammalian Cells", Analytical Biochemistry, vol. 120, No. 2, 1982, pp. 282-288.

Tai, et al., "Automatic microfluidic platform for cell separation and nucleus collection", vol. 9, No. 4, 2007, pp. 533-543.

European Office Action dated Dec. 22, 2014 in European Application No. 10 783 380.8.

* cited by examiner

METHOD FOR PREPARING PROTEIN, DNA, AND RNA FROM CELL

TECHNICAL FIELD

The present invention relates to a method for preparing a protein, DNA, and RNA from a cell. Particularly, the present invention relates to a method for preparing, from one cell, at least two selected from the group consisting of a protein, DNA, and RNA. The present invention further relates to a method for conveniently and efficiently preparing a nucleic acid or the like from a cell.

BACKGROUND ART

Collectively areas of research, such as genomics, transcriptomics, and proteomics, or areas of integrated research thereof have been referred to as "omics" or "omics research" in recent years.

The genomics targets genomic DNA. The genomic analysis discovers DNA polymorphisms or factors contributing to genetic disease and reveals the association of disease with such polymorphisms, mutations, or factors.

The transcriptomics targets transcribed RNA. The transcriptomic analysis reveals the correlation of gene expression levels with disease, biological phenomena, or the like.

Furthermore, the proteomics targets proteins. The proteomic analysis offers findings on the association of protein expression levels with disease, biological phenomena, or the like, based on the identification and quantification of particular proteins.

All of these pieces of biological information obtained by genomics, transcriptomics, proteomics, and metabolomics (which is based on metabolites in plasma) are comprehensively analyzed to provide for efficient research. Furthermore, the obtained findings can be used very effectively in basic research or in disease diagnosis or treatment. Thus, a breakthrough in omics research is expected.

Moreover, it has been reported in recent years that the molecular profiles of peripheral blood cells reflect physiological and pathological transformation occurring in various tissues in the body. Along with this, diagnosis has been attempted by the analysis of proteins, metabolites, and gene expression in blood cells.

Meanwhile, for example, the isolation of DNA, RNA, and proteins from, for example, blood cells, involves initially recovering the blood cells and further requires subsequent complicated procedures. DNA targeted by genomic analysis is present in nuclear membranes; RNA targeted by transcriptomic analysis is present in cytoplasmic ribosomes; and proteins targeted by proteomic analysis are present in cell membranes, cytoplasms, nuclear membranes, and so on. Therefore, to prepare DNA, RNA, and proteins from cells, in general, these components are prepared through different routes under the present circumstances. Since the preparation of, for example, nucleic acids (DNA or RNA), targets only these nucleic acids, other components, particularly, proteins, are often denatured with a strong denaturant. Moreover, their respective preparations are complicated. A convenient and efficient extraction method has not been developed yet.

A conventional method for preparing nucleic acids will be described below. In the conventional preparation of nucleic acids, cells are first recovered and then lysed by physical treatment or treatment with a surfactant. Then, impurities are removed therefrom using an organic solvent such as water-saturated phenol or chloroform. In this method, in general, a nucleic acid fraction in the solution is subsequently precipitated with alcohol and further purified, if necessary, by column chromatography (Lectures on Biochemical Experiments 2 (Tokyo Kagaku Dojin), "Nucleic Acid Chemistry I" p. 74-80, p. 262-270, Gene Manipulation Manual (Kodansha Ltd.), p. 20-23, 1982).

In this method, proteins in the cell membranes are often denatured due to the surfactant treatment for lysing the cells. For example, cationic, anionic, nonionic, and amphoteric surfactants are used as the surfactant. On the other hand, proteins in the cytoplasms are also denatured by the phenol or chloroform treatment in the conventional method. This phenol or chloroform treatment requires the procedure of separating an organic solvent layer and a nucleic acid layer by centrifugation or the procedure of performing column chromatography. Moreover, phenol is toxic and causes chemical burn upon contact with the skin. Chloroform is anesthetically active. Therefore, this method also has the disadvantage that the handling or disposal method of these chemicals is an issue.

Furthermore, RNA preparation requires suppressing decomposition, because RNA is exceedingly easily decomposed by RNase. Therefore, a generally adopted method includes denaturing proteins using an RNase inhibitor or a chaotropic agent and then separating an RNA fraction based on adsorption to silica. In fact, many commercially available kits adopt this method. The chaotropic agent generates chaotropic ions (monovalent anions having a large ionic radius) when added to an aqueous solution and has the effect of increasing the water solubility of hydrophobic molecules. Specific examples thereof include alkali iodide, guanidine thiocyanate, alkali metal salts of perchloric acid, alkali metal salts of trifluoroacetic acid, alkali metal salts of trichloroacetic acid, and alkali metal salts of thiocyanic acid. These chaotropic agents in use do not require using organic solvents such as phenol and chloroform and therefore eliminate the problem associated with the handling of phenol or chloroform. However, even when the chaotropic agents are used, the fact remains that proteins are strongly denatured.

Next, DNA and RNA separation will be described. DNA is present in nuclear membranes, and RNA is present in cytoplasms. Thus, cells are treated under conditions that lyse cell membranes but do not lyse nuclear membranes to recover only the nuclei. As a result, DNA and RNA can be separated. As described above, ionic surfactants are used for lysing cell membranes. Of the ionic surfactants, particularly, anionic surfactants lyse nuclear membranes and nucleoproteins and as such, cannot be used in the DNA and RNA separation.

A method for lysing only cell membranes without lysing nuclear membranes is disclosed in New Lectures on Biochemical Experiments 2 (ed., by The Japanese Biochemical Society), Nucleic Acid I, Separation and Purification, p. 49. In this method, cells are treated with NP-40 or Triton X-100 at a final concentration of 0.3%. Furthermore, conditions for nuclear separation described therein involve a Triton X-100 concentration of 0.3% or 1%, an NP40 concentration of 0.1 to 0.5%, and a Tween 20 concentration of 1%.

However, as seen from results of similar experiments conducted by the present inventors, the obtained RNA sample may be contaminated with DNA, and the nuclear membranes are partially dissolved. Particularly, this tendency was apparent for a small number of cells. Therefore, it is difficult for the above method of New Lectures on Biochemical Experiments 2 to obtain a DNA or RNA sample uncontaminated with the other component.

Moreover, Japanese Patent Application Laid-Open No. 2006-51042 discloses a method including directly subjecting cytoplasmic mRNA to RT-PCR, wherein only cell membranes are dissolved without dissolving nuclear membranes to separate cytoplasmic mRNA. Specifically, the disclosed method includes suspending cultured cells for approximately 5 minutes in a solution containing 0.1 to 0.5% NP-40 as a surfactant in 10 mM tris-HCl (pH 7.6) and then centrifuging (1200 g, 5 min) the suspension to recover a nuclear fraction as precipitates. However, this method is merely intended to reduce the amount of contaminating DNA for enhancing RT-PCR efficiency and does not completely separate DNA and RNA.

Disclosures of other nuclear separation methods can be referred to Patent Japanese Patent Application Laid-Open No. H6-205676 and U.S. Pat. No. 6,718,742. Japanese Patent Application Laid-Open No. H6-205676 discloses a method including: adding a buffer solution containing 0.32 M saccharose, 5 mM magnesium chloride, 1% Triton X-100, and 0.2% sodium azide to the whole blood; then recovering nuclei by centrifugation at 12000 rpm for 20 seconds; further lysing nuclear membranes and nucleoproteins by treatment with a surfactant and a protease; and then separating DNA strands by contact with a chaotropic agent.

Moreover, U.S. Pat. No. 6,718,742 discloses that a solution containing 1% Tween 20 in 10 mM ammonium bicarbonate (pH 9.0) is effective for nuclear separation.

As described above, the conventional methods hardly detected, identified, or quantified a nucleic acid and a protein from one sample. Moreover, all of these methods were complicated and did not prepare a nucleic acid or the like conveniently and efficiently from a cell.

DISCLOSURE OF THE INVENTION

An object of the present invention is to provide a method for preparing DNA, RNA, and a protein from one cell and a method for conveniently and efficiently preparing a nucleic acid or the like from a cell.

The present inventor conducted diligent studies to attain the object and consequently devised a method which involves nuclear separation from cells and subsequent protein or nucleic acid separation. The present inventor further found that this method can secure higher recovery and purity than those of conventional preparation methods, which include lysing the whole cells. Moreover, the present inventor devised a method including using two filters connected to each other to prepare a nucleic acid or the like from cells in a liquid such as blood. As a result, the present invention has been completed.

Specifically, the present invention provides a method for preparing, from one cell, at least two selected from the group consisting of a protein, DNA, and RNA, including performing nuclear and cytoplasmic separation and then extracting at least two of a protein, DNA, and RNA.

Moreover, the present invention provides a method for preparing, from one cell, at least two selected from the group consisting of a protein, DNA, and RNA, including: treating the cell with a surfactant solution that lyses cell membranes but dose not lyse nuclear membranes; and passing the treated cell solution thus obtained through a filter including a membrane having such a pore size as to be impenetrable to nuclei but allow cytoplasmic ribosomes to pass therethrough.

Moreover, the present invention provides a cell preparation method, including:
using a first filter having a pore size that is impenetrable to cells but allows nuclei to pass therethrough to capture a cell on the first filter; injecting a solution containing a surfactant onto the first filter to cause reaction with the cell captured on the filter; connecting a second filter having a pore size impenetrable to nuclei to the first filter such that the second filter is placed subsequent to the first filter; and passing a liquid through the first filter and the second filter by pressure injection to capture the nucleus on the second filter while passing a cytoplasmic fraction therethrough surfactant.

Moreover, the present invention provides a method for preparing, from one cell, at least two selected from the group consisting of a protein, DNA, and RNA, including: treating the cell with a surfactant solution that lyses cell membranes but dose not lyse nuclear membranes; and passing the treated cell solution thus obtained through such a pore as to be impenetrable to cells but allow nuclei to pass therethrough.

The present invention achieved the preparation of at least two selected from the group consisting of a protein, DNA, and RNA from one cell. The present invention not only requires a much smaller amount of samples than that required for conventional preparation on a component-by-component basis, but also eliminates operation such as centrifugation, which requires experience and skills. Thus, highly reproducible samples suitable for omics can be prepared conveniently in a short time.

Moreover, since each component can be prepared in a short time from cell collection, each component is less susceptible to denaturation or decomposition. As a result, facilitation of subsequent analysis can be expected.

Furthermore, the present invention can provide an approach friendly to work environments, workers, and the environment without the use of toxic solvents such as phenol and chloroform or corrosive solvents such as chaotropic agents.

Further features of the present invention will become apparent from the following description of exemplary embodiments with reference to the attached drawings.

BRIEF DESCRIPTION OF THE DRAWINGS

FIG. 5A illustrates the results obtained using $10^5$ cells, and FIG. 5B illustrates the results obtained using $10^4$ cells;

BEST MODES FOR CARRYING OUT THE INVENTION

Figure 1:
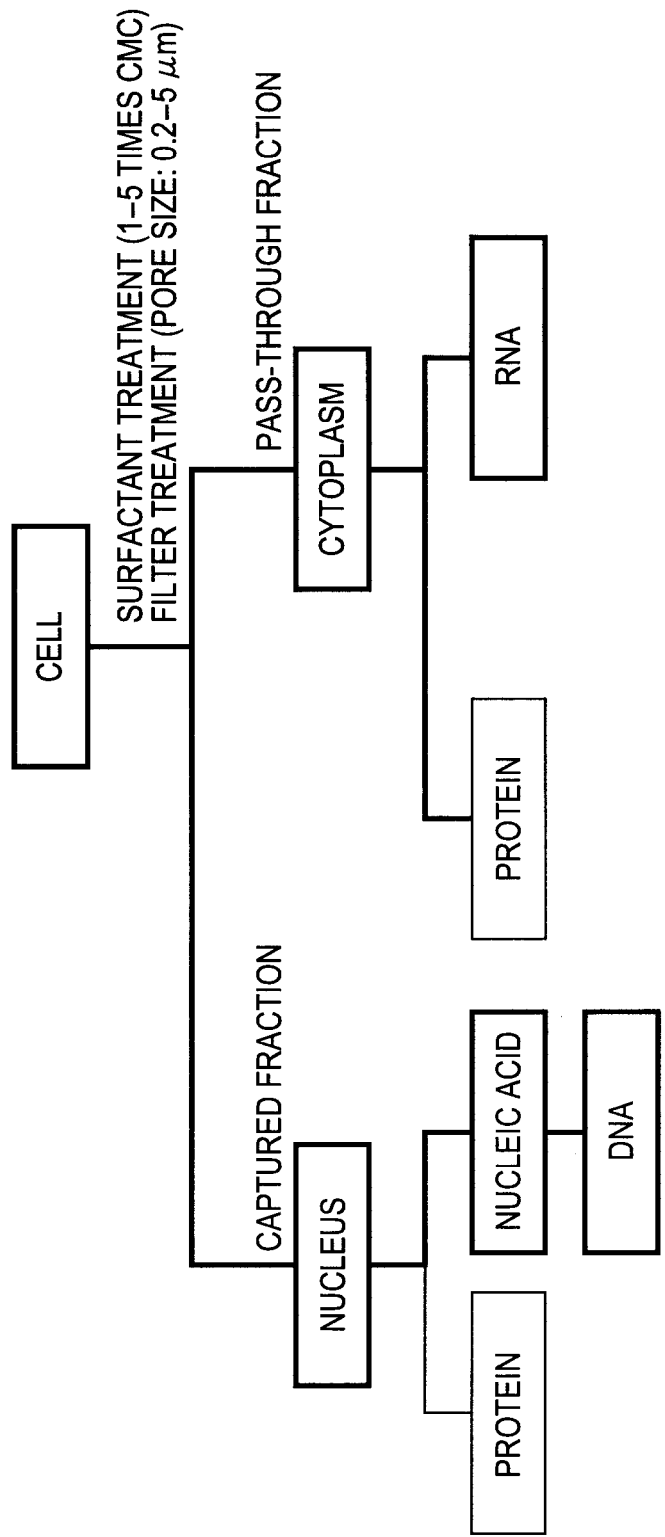
FIG. 1 is a flow chart of the present invention.

The present invention provides a method for preparing, from one cell, at least two selected from the group consisting of a protein, DNA, and RNA, including performing nuclear and cytoplasmic separation and then extracting at least two of a protein, DNA, and RNA.

The present invention further provides a method for preparing, from one cell, at least two selected from the group consisting of a protein, DNA, and RNA, including: treating the cell with a surfactant solution that lyses cell membranes but dose not lyse nuclear membranes; and passing the treated cell solution thus obtained through a filter including a membrane having such a pore size as to be impenetrable to nuclei but allow cytoplasmic ribosomes to pass therethrough.

The preparation of at least two selected from the group consisting of a protein, DNA, and RNA from one cell refers to preparing at least two selected from the group consisting of a protein, DNA, and RNA from a cell or a cell group in a single sample. Conventionally, to prepare a protein, DNA, and RNA from the same cell type, in general, even the cells of the same type were separately prepared into cell samples for separation on a component-by-component basis.

Conventional centrifugation or ethanol precipitation based on gravity or solubility is largely influenced by the environment where the cells are placed (e.g., the number of cells, salt concentrations, glucose levels, for example, for blood). The present invention provides for stable preparation with high reproducibility, because separation is performed using a filter appropriate for an organ size.

Furthermore, the conventional techniques required a plurality of runs of, for example, centrifugation or ethanol precipitation manually performed by workers. Mechanization of these procedures, i.e., automatic preparation, was practically difficult. By contrast, in the present invention, pretreatment is performed using a filter. Therefore, automation is achieved by incorporating continuous operation using combined filters into the treatment procedure. Furthermore, its application to microfluidic techniques also achieves device orientation.

Moreover, according to the present invention, every procedure from the recovery of cells in samples such as blood to the preparation of nucleic acids or proteins can be performed conveniently. Therefore, particularly, for mRNA, its extraction can be performed more efficiently than the conventional methods. Since mRNA is easily decomposed by RNase present in the environment, its expression analysis was difficult. However, according to the present invention, mRNA can be extracted in a few minutes. Therefore, for example, blood can be pretreated immediately after blood collection. Thus, highly reproducible, undecomposed samples can be obtained. Moreover, according to the present invention, nuclear gene expression can be evaluated after separation into nuclear and cytoplasmic fractions. As a result, highly precise diagnosis is achieved by detailed expression analysis.

The cell targeted by the present invention is not limited by any means as long as the cell has a nucleus. The present invention targets every cell such as animal cells, plant cells, bacterium-, fungus-, or tissue-derived cells, cultured cells, blood-derived cells (e.g., white blood cells), stem cells (e.g., ES cells), genetically modified cells, and induced stem cells (e.g., iPS cells). These targeted cells can be separated and concentrated in advance. For example, blood contains a large number of red blood cells. Therefore, when the targeted cells are white blood cells, these white blood cells can be separated from blood. Specifically, a method can be adopted, which includes obtaining a buffy coat (white blood cell fraction) by centrifugation or centrifuging white blood cells as precipitates after hemolysis operation. The hemolysis operation lyses anucleate red blood cells rich in blood so as to facilitate the subsequent separation of white blood cells by centrifugation. For example, ammonium chloride, ammonium oxalate, or saponin is used as a hemolytic agent.

In the present invention, treatment with a surfactant solution that lyses cell membranes but dose not lyse nuclear membranes can be performed as a method for the nucleic and cytoplasmic separation.

Examples of the surfactant can include the followings: cationic surfactants such as dodecyltrimethylammonium bromide, dodecyltrimethylammonium chloride, and cetyltrimethylammonium bromide; anionic surfactants such as sodium dodecyl sulfate (SDS), sodium cholate, sodium dodecyl cholate, and N-lauroylsarcosine sodium; nonionic surfactants such as polyoxyethylene octyl phenyl ether (e.g., Rohm and Haas Company trade name: Triton X-100), polyoxyethylene sorbitan monolaurate (e.g., Kao Corp. trade name: Tween 20), polyoxyethylene sorbitan monooleate (e.g., Kao Corp. trade name: Tween 80), n-octyl-β-D-glucoside, n-octyl-β-D-glucopyranoside, n-octylthio-β-D-thioglucopyranoside, octylphenyl-ethoxyethanol (e.g., trade name: Nonidet P-40 (NP40)), polyethylene-lauryl ester (e.g., trade name: Brij 35), and polyethylene glycol hexadecyl ester (e.g., trade name: Brij 58); and amphoteric surfactants such as 3-[(3-cholamidopropyl)dimethylammonio]-1-propanesulfonate and phosphatidylethanolamine.

Among these surfactants, the anionic surfactant is known to lyse nuclear membranes and nucleoproteins. The cationic surfactant is also likely to apply a bias to the original biological distribution, through its interaction with the charges of proteins or genes. Thus, the nonionic surfactant can be used for finally preparing all proteins, genes, and low-molecular-weight compounds exhaustively. Particularly, the nonionic surfactant is also suitable for the selective separation of cell membranes and nuclear membranes. However, the present invention is not limited to the use of only the nonionic surfactant. After identification of the substance to be examined, the anionic surfactant or the cationic surfactant may be used appropriately in a portion of the process as a more efficient preparation method. Moreover, the surfactant can have a concentration not lower than its CMC (critical micelle concentration) and within 10 times its CMC (critical micelle concentration). Particularly, the surfactant can have a concentration 1 to 5 times its CMC (critical micelle concentration).

The treatment of the cell with the surfactant used in the present invention may be performed by suspending cells recovered by centrifugation or the like in the surfactant solution or by suspending the cells in saline or the like to adjust the amount of the surfactant to the desired final concentration. However, the surfactant concentration in the cell solution is temporarily made nonuniform by the addition of the surfactant at a high concentration. Thus, the high-concentration portion might lyse not only cell membranes but also nuclear membranes. Therefore, the method of the present invention can further include mixing the cell solution with the surfactant uniformly dispersed by stirring or the like such that the partial high-concentration region is absent. Moreover, the surfactant concentration in the mixed solution can also be prevented from exceeding the concentration described above by using a solution of the surfactant at a concentration 1 to 5 times its CMC in advance.

Moreover, the cell recovery is performed by recovering cells by centrifugation as described above. In addition, the cell recovery may be performed by: passing cells through a filter having a pore size smaller than the cell size to capture the cells on the filter; then dissociating the cells from the filter; and recovering the cells as a suspension.

Moreover, to perform nucleic and cytoplasmic separation, cells are treated with the surfactant solution, and the treated solution can further be subjected to separation using a filter.

The material and pore size of the filter for separation are not particularly limited. The filter can have such a pore size as to be impenetrable to nuclei but allow organs (e.g., cytoplasmic ribosomes) to pass therethrough.

Phagocytes have a size of 7 μm or larger (neutrophils) or 6 μm or larger (lymphocytes or macrophages). The nucleus present therein has a size of 6 μm or smaller. Therefore, the filter pore size that recovers nuclei and allows cytoplasms to pass therethrough can be 5 μm or smaller, which permits sufficient separation therefrom.

Moreover, ribosomes themselves contained in cytoplasms have a diameter on the order of 20 nm. However, these ribosomes are often found as a cluster of 10 to 20 ribosomes bound as a polysome to mRNA. Therefore, ribosomes to be passed through the filter have a size of 0.1 μm to 0.2 μm. Thus, the filter can have a pore size of 0.2 μm to 5 μm, particularly, 0.2 to 1 μm. The filter can be made of any hydrophilic material. For example, polyvinylidene fluoride, polyether sulfone, polycarbonate, polytetrafluoroethylene, and cellulose-mixed ester can be used.

Moreover, the preparation method of the present invention is a method for preparing, from one cell, at least two selected from the group consisting of a protein, DNA, and RNA, including: treating the cell with a surfactant solution that lyses cell membranes but dose not lyse nuclear membranes; and passing the treated cell solution thus obtained through such a pore as to be impenetrable to cells but allow nuclei to pass therethrough.

By these treatments, extranuclear substances (e.g., cell membranes) that have been lysed by the surfactant but still attached to the nuclei can be dissociated favorably from the nuclei. This can promote homogenization of the solution.

Moreover, the preparation method of the present invention can further include homogenizing the treated cell solution, particularly before the nucleic and cytoplasmic separation. The homogenization of the treated cell solution refers to crushing solid matter into sufficiently fine pieces to provide for the uniform state of the contents.

The homogenization of the treated cell solution can be performed by passing the treated cell solution through an injection needle plural times. In this case, the gage of the injection needle is not particularly limited. For example, 21G (inside diameter: 0.57 mm) or 25G for tuberculin (inside diameter: 0.32 mm) can be used suitably.

Alternatively, the homogenization of the treated cell solution can also be performed by passing the treated cell solution through a channel having a pore size that is impenetrable to cells but allows nuclei to pass therethrough. Examples of such a channel can include microchannels and filters. Examples of the filters can include filters having a pore size of 1.0 μm to 8.0 μm, particularly a pore size of 1.0 to 5.0 μm.

In this way, the surfactant-treated cell solution can be passed, before the filter separation into nucleus and cytoplasm solutions, through a channel having a pore size that is smaller than the cell size and larger than the intracellular nucleus size so as to achieve homogenization that permits favorable separation of nucleus and cytoplasm solutions. This channel having a pore size that is impenetrable to cells but allows nuclei to pass therethrough may be connected to the filter including a membrane having such a pore size as to be impenetrable to nuclei but allow cytoplasmic ribosomes to pass therethrough.

The present invention also provides a cell preparation method, including: using a first filter having a pore size that is impenetrable to cells but allows nuclei to pass therethrough to capture a cell on the first filter; injecting a solution containing a surfactant onto the first filter to cause reaction with the cell captured on the filter; connecting a second filter having a pore size impenetrable to nuclei to the first filter such that the second filter is placed subsequent to the first filter; and passing a liquid through the first filter and the second filter by pressure injection to capture the nucleus on the second filter while passing a cytoplasmic fraction therethrough.

The cell described here is a cell contained in a liquid. Specifically, possible cells are, for example, cells contained in blood, lymph, or other body fluids, liquid-cultured cells, or cells suspended in a medium, a buffer solution, or other solutions. The type of the cell is not limited by any means as long as the cell has a nucleus. Examples of the cell include those exemplified above. However, in light of the object of the present invention, blood may be targeted as the liquid. Particularly, white blood cells in blood can be used as a target.

Examples of the first filter having a pore size that is impenetrable to cells but allows nuclei to pass therethrough can include filters having a pore size of 1.0 to 8.0 μm, particularly, a pore size of 1.0 to 5.0 μm. The filter can be made of any hydrophilic material. Examples thereof include those exemplified above.

Moreover, the capture of the cell on the first filter refers to allowing the cell to remain on the filter, for example, as a result of charging a cell-containing solution onto the filter and passing the cell through the filter by pressure application using a syringe or a pump.

The injection of a solution containing a surfactant to cause reaction with the cell captured on the filter refers to bringing a surfactant solution that lyses cell membranes but dose not lyse nuclear membranes, into contact with the first filter by injection to treat the cell captured on the first filter with the surfactant upon contact. Examples of the surfactant can include those exemplified above. Moreover, the surfactant can have a concentration not lower than its CMC (critical micelle concentration) and within 10 times its CMC (critical micelle concentration). Particularly, the surfactant can have a concentration 1 to 5 times its CMC (critical micelle concentration). During the reaction, stirring or the like can also be performed appropriately to promote the reaction.

Examples of the second filter having a pore size impenetrable to nuclei can include filters having a pore size of 0.2 μm to 5.0 μm, particularly, a pore size of 0.2 μm to 1.0 μm. The filter can be made of any hydrophilic material. Examples thereof include those exemplified above.

The connection of the second filter having a pore size impenetrable to nuclei to the first filter such that the second filter is placed subsequent to the first filter refers to connecting the second filter downstream of the first filter. In this case, the first filter and the second filter may be connected via a stopcock, a syringe, a tube, a filter, or other instruments for connection. The first filter and the second filter connected with each other may be referred to herein as a "double filter".

The passing of a liquid through the first filter and the second filter by pressure injection refers to injecting a buffer solution, a medium, saline, or other solutions from upstream of the first filter and the second filter connected with each other, i.e., from upstream of the first filter, under pressure. As a result, the nucleus in the cell that has been captured on the first filter and whose cell membrane has been lysed is captured on the second filter, while a cytoplasmic fraction passes through the second filter, as described above. By this procedure, nuclei and cytoplasms are separated.

The passing through the second filter is also expected to have the effect of homogenizing the treated cell solution. Specifically, since nuclear membranes are more robust than cell membranes, cell membranes insufficiently lysed by the surfactant treatment are sufficiently lysed by passing through the second filter. As a result, nuclei and cytoplasms are separated more efficiently.

The two filters used in the present invention can be approximately equal in size, or the second filter has a smaller area. This is because the homogenization effect is enhanced by resistance occurring to an extent during the pressure application. However the area ratio therebetween can be 50% or lower.

The analysis of gene expression in cells is very useful. On the other hand, nuclear mRNA and cytoplasmic mRNA differ in their functions and must be separated for evaluation in some cases. In the present invention, nuclear gene expression can be evaluated after separation into nuclear and cytoplasmic fractions. As a result, highly precise diagnosis is achieved by detailed expression analysis.

Moreover, cells contained in a liquid may be separated by centrifugation. However, in such a case, the cellular fraction coexists with the liquid components. To accurately set the surfactant concentration for nucleic and cytoplasmic separation, contamination with the liquid largely influences reproducibility or yields. Moreover, when the sample is blood, a hemolytic agent must be used, which might however have adverse effect on sample preparation. A possible method to completely remove the contaminating liquid utilizes a filter in cell separation. However, the procedure of dissociating, from the filter, white blood cells captured on the filter may be added for suspending the cell spheres in the surfactant solution. Its efficiency determines reproducibility. To solve this problem, the surfactant can be reacted with the cell on the filter without dissociating the cell captured on the filter. This eliminates the problem.

Furthermore, the cytoplasmic fraction that has passed through the two filters can be reacted with an oligo(dT)-bound support. As a result, mRNA can be recovered conveniently.

In the present invention, as a result of diligent studies, it was found that mRNA in the cytoplasmic fraction is present separately from proteins, at an appropriate surfactant concentration and also found that by use of the poly(A) of the mRNA, the mRNA can be recovered directly using the oligo(dT) support.

As a result, the conventional methods required 10 or more steps for extracting a total RNA fraction and subsequent mRNA recovery using oligo(dT) beads, whereas the present invention provided for a very convenient method requiring less time, which merely involves passing the surfactant solution through the two cell-immobilized continuous filters and binding the pass-through fraction to the oligo(dT) beads for recovery.

According to this method, the cytoplasm solution separated through the filter from the nucleus is reacted directly with the oligo(dT)-bound support without extracting an RNA fraction. As a result, mRNA can be recovered efficiently in an exceedingly short time.

The concentration of the surfactant used here is appropriately not lower than its CMC (critical micelle concentration) and within 10 times its CMC (critical micelle concentration), particularly, 1 to 5 times its CMC. At a high surfactant concentration, nuclei are lysed, resulting in a reduced yield due to DNA blocking the filter pores. In this context, the oligo(dT)-bound support is a support bound with oligo(dT). Examples thereof can include magnetic beads and resin beads.

Furthermore, the cytoplasmic fraction that has passed through the two filters can be used in protein analysis. Furthermore, a fraction that has been unbound with the oligo(dT) can be used in protein analysis. The analysis described here is not particularly limited and refers to, for example, quantification of proteins, quantitative or qualitative analysis of particular proteins, or exhaustive analysis of proteins.

The present invention also provides a kit or a microdevice configuration for performing the method described above.

Figure 2:
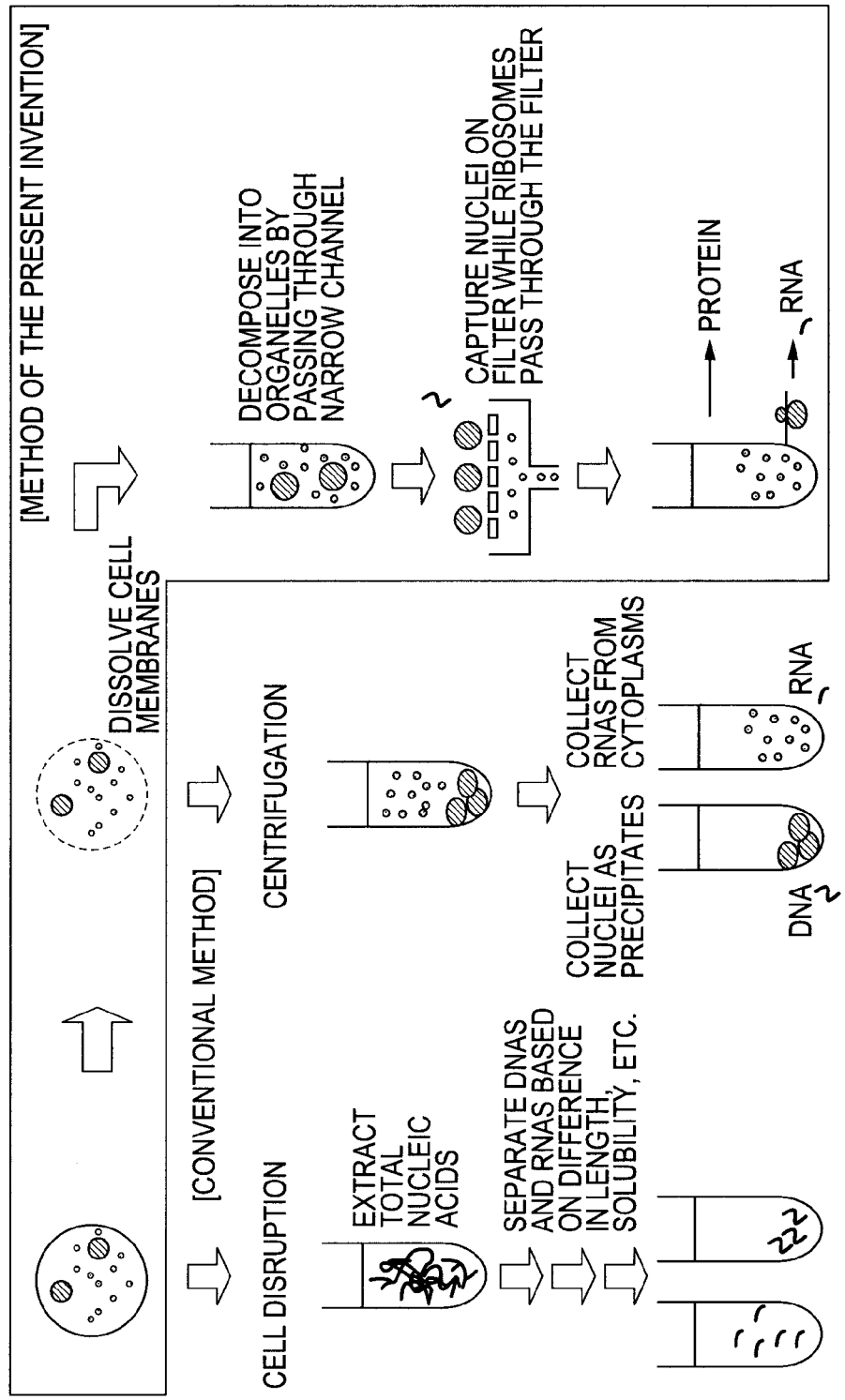
FIG. 2 is a conceptual diagram of the present invention.
Figure 3:
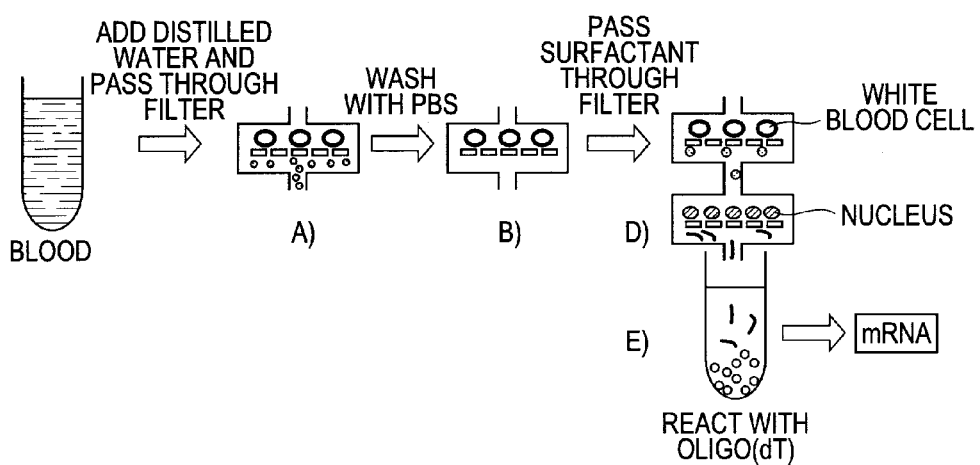
FIG. 3 is a conceptual diagram of the present invention.

FIGS. 1, 2, and 3 illustrate the principle and procedures of the present invention. FIG. 1 will be described. Cells are treated with a surfactant solution that lyses cell membranes but dose not lyse nuclear membranes. The resulting solution is further separated into a filter-captured fraction and a pass-through fraction by passing through a filter including a membrane having such a pore size to be impenetrable to nuclei but allow cytoplasmic ribosomes to pass therethrough. The filter-captured fraction is nuclei, and the pass-through fraction contains cytoplasms. Nucleic acids can be extracted from the nuclei, and DNA can be extracted from the nucleic acids. On the other hand, protein components and RNA can be obtained from the cytoplasms.

Next, FIG. 2 will be described. FIG. 2 is a diagram illustrating the principle of nuclear and cytoplasmic separation. The method of the present invention does not adopt cell lysis or centrifugation performed in the conventional methods. In the method of the present invention, cell membranes are lysed without lysing nuclear membranes, and the resulting solution is passed through a filter to capture the nuclei on the filter while ribosomes and cytoplasms are obtained as a pass-through fraction.

FIG. 3 is a conceptual diagram illustrating a method with peripheral blood as an example, which includes using a first filter and a second filter to separate white blood cells and nuclei from cells in peripheral blood.

In this diagram, peripheral blood is first hemolyzed in a hypotonic solution supplemented with distilled water or the like. This solution is passed through a filter (first filter) having a pore size capable of capturing white blood cells to recover only white blood cells. The suitable range of the pore size of the first filter is 1.0 μm to 8.0 μm and can be 3.0 μm to 5.0 μm. Then, the filter can be washed with saline or a buffer solution to wash off components that become a noise in expression analysis, such as globin in red blood cells. In principle, cells captured on the filter may be recovered temporarily and subjected to subsequent treatment. In actuality, the whole amount of the cells is difficult to completely recover, resulting in poor quantitative performance. Thus, in the present invention, the cells on the filter are reacted with a surfactant.

Next, the surfactant-treated solution is passed through a second filter having a pore size that is smaller than the cell size and larger than the nucleus size. By passing through the filter pores under pressure, cell membranes dissolved by the surfactant are lysed, while nuclear membranes that are undissolved by the surfactant and are relatively robust against physical stimulation such as pressure application pass through the filter pores without being lysed. As a result, nuclei and cytoplasms are separated such that only the nuclei are captured on the second filter while the cytoplasms pass through the second filter. In this case, the treated solution is homogenized by passing through the second filter to completely lyse the cell membranes. This effect was found by the present inventors by focusing on the fact that nuclear membranes are more robust against physical stimulation than cell membranes. The cell membranes may be lysed by passing through an injection needle. In such a case, since an injection needle having an inside diameter of several hundreds of microns is several tens of times thicker than the cell size, the degree of cell membrane lysis varies depending on speeds of injection needle's to-and-fro movements or cell concentrations. However, according to the method of the present invention, the cell membranes could be lysed more stably.

The second filter has a pore size that is smaller than the cell size and larger than the nucleus size. The pore size is specifically 1.0 μm to 8.0 μm and can be 1.0 μm to 5.0 μm. In the present diagram, the method using a filter is described. However, any of other methods including moving cells through space narrower than the cell size can be used, such as a method using microfluidics.

The present invention will be further described with reference to Examples shown below.

EXAMPLES

A conventional nuclear separation method is described in Lectures on Biochemical Experiments 2 (Tokyo Kagaku Dojin),"Nucleic Acid Chemistry I" p. 74-80, p. 262-270. In this method, cells are treated with 0.3% NP40 or 0.3% Triton X-100 to dissolve the cell membranes while preserving the nuclear membranes. Then, a nuclear fraction is recovered by low-speed centrifugation. However, this method cannot completely preserve all the nuclei, although the nuclei can be recovered reliably. In some cases, some nuclei are observed to be lysed, resulting in leakage of DNA. This method is suitable for the purpose of recovering only intact nuclei for nuclear or nuclear membrane research and is however inappropriate for the purpose of completely fractionating nuclei and cytoplasms, because the cytoplasms may be contaminated with the nuclear components. Other surfactants such as Tween 20 are also disclosed. However, all of the disclosures merely specify a preferable surfactant concentration region by wt %, regardless of surfactant types, and make no mention of surfactant selection or grounds for determining the concentration of the surfactant. Moreover, none of these disclosures make a mention of the association of concentrations of various surfactants with their CMCs. Thus, the determination of conditions for nuclear and cytoplasmic separation requires more detailed study and trial and error, including evaluation methods thereof.

The present inventors prepared a dilution series of a surfactant in Examples below and observed cell morphology at each concentration of the surfactant. The present inventors further predicted a concentration at which cell membranes are dissolved with nuclear membranes preserved, based on the amount of total RNA extracted from cytoplasms, the amount of contaminating DNA, and the quality of rRNA occupying the large majority of total RNA as evaluation criteria. First, the interaction between various nonionic surfactants and cells was grasped by the morphological observation of the cells in solutions containing varying concentrations of the surfactants. Specifically, the interaction between various surfactants and cells was confirmed by the morphological observation of the cells in this environment. As a result, it was found that the cells exhibited three morphologies with change in the concentration of any of the surfactants. These three morphologies were predicted to be three states: (i) a state where both the cell membranes and the nuclear membranes are preserved; (ii) a state where the cell membranes are dissolved while the nuclear membranes are preserved; and (iii) a state where both the cell membranes and the nuclear membranes are dissolved. The surfactant concentration at which the cells exhibit the state (ii) largely differs depending on surfactant types. It was found that the lowest surfactant concentration at which the state (ii) could be detected, during shift from the low to high regions of the concentration, exceedingly favorably correlated with the CMC (critical micelle concentration) of each surfactant. The CMC (critical micelle concentration) refers to the minimal concentration of each surfactant at the interface necessary for forming a micelle of the surfactant. The CMCs of typical surfactants are 0.015% (Triton X-100), 0.018% (NP40), and 0.007% (Tween 20).

As a result of Examples, a surfactant concentration suitable for nuclear separation was determined to be much lower than that as a nuclear separation condition in other methods disclosed as the prior art. In the prior art, the surfactants are used at concentrations corresponding to 0.3% for Triton X-100, which is 20 times its CMC, 0.1 to 0.5% for NP40, which are 5 to 27 times its CMC, and 1% for Tween 20, which is 143 times its CMC. Even given that the surfactants differ in their properties, all these concentrations are 0.1 to 1% (particularly, 0.1 to 0.5% in most cases) in simple indication in wt % and are however indicated in a wider variety of numeric values from 5 times to 143 times from the viewpoint of CMC.

In the present Examples, cell membranes start to be dissolved by the treatment of the cells with a surfactant at a concentration higher than its CMC, and the dissolution of their nuclear membranes is not observed until a surfactant concentration is about 10 times its CMC. Therefore, a surfactant concentration suitable for dissolving cell membranes was determined to be a concentration equal to or lower than 10 times its CMC.

The region of surfactant concentrations at which only cell membranes are dissolved while nuclear membranes are not dissolved differs depending on surfactant types. In most cases, the cells exhibit the state (ii) at a surfactant concentration up to 10 times the CMC and are placed at risk of solubilizing the nuclear membranes at a surfactant concentration equal to or higher than 10 times the CMC. Research aimed at nuclear membranes is intended to prevent contamination with cytoplasmic components. For preventing the contamination of cytoplasms with nuclear DNA, it is important to completely preserve nuclear membranes. Thus, it was shown that the appropriate setting of a surfactant concentration was important. Hereinafter, Examples will be described in more detail. In Examples below, concentrations indicated in % refer to concentrations by wt %, unless otherwise specified.

Example 1

Cultured Cells; K562 cells were grown in RPMI 1640 containing 10% FBS, 500 units/ml penicillin, and 500 μg/ml streptomycin and subcultured twice a week at a ratio of approximately 1:10. The cells were recovered, then washed with a PBS solution, and then suspended at a concentration of $10^6$ cells/ml in a PBS solution.

Surfactant; PIERCE Surfact-Pak Surfactant Sampler Kit was purchased, and 10%, 1%, 0.1%, and 0.01% solutions of each surfactant were prepared.

The surfactant solutions and PBS were added to each well of a microtiter plate to prepare a dilution series of each surfactant (12 dilutions of 0.0025, 0.005, 0.0075, 0.025, 0.05, 0.075, 0.25, 0.5, 0.75, 2.5, 5, and 7.5%; 100 μl each). To each of these surfactant solutions, 100 μl of the cell suspension (approximately $10^6$ cells/ml) was added, and the cells and the surfactant were mixed by gently shaking the microtiter plate.

Then, the morphology of the cells in each well was observed under a phase-contrast microscope. In this context, cells nonsupplemented with the surfactant were used as a control.

The results are shown in Table 1. In the absence of the surfactant or at an exceedingly low concentration thereof, the cells have a clear outline and contain, in the central part, a portion regarded as a nucleus differing in contrast therefrom (indicated in + in Table 1). With rise in surfactant concentration, the cell outline, albeit obscure, can be detected (not shown in Table 1), although the contrast of the central part is reduced. At a further higher surfactant concentration, the outlines of the cells and the nuclei cannot be differentiated from their surrounding solution, and the cells are incorporated in the surrounding solution and thus, cannot be detected (indicated in – in Table 1). Along with this change in cell morphology, the cells in a region less influenced by the surfactant tend to aggregate with each other and localize. However, these cells are dispersed with rise in surfactant concentration.

These states were predicted to be three states: (i) a state where both the cell membranes and the nuclear membranes are preserved (indicated in + in Table 1); (ii) a state where the cell membranes are dissolved while the nuclear membranes are preserved (not shown in Table 1); and (iii) a state where both the cell membranes and the nuclear membranes are dissolved (indicated in – in Table 1). The surfactant concentration at which the cells exhibit the state (ii) largely differs depending on surfactant types. It was found that the point (surfactant concentration) at which the contrast at the cell center starts to become obscure, during shift from the low to high regions of the concentration, very highly correlates with the CMC (critical micelle concentration) value of each surfactant. This tendency was also reproduced at varying numbers of cells. However, when Triton X-114 was used, the cells were unsuccessfully observed due to its high cloud point. Moreover, since the Tween series have exceedingly low CMC, their dilution precision could not be secured.

This phenomenon is presumably because, for example, the cell membranes were dissolved at a surfactant concentration around the CMC, and as a result, the cell morphology was deformed such that the bulge of the nuclei was flattened.

Example 2

If the prediction described above is correct, it is expected that the low-speed centrifugation of the solution of the cells in the state (ii) precipitates the nuclei while a cytoplasmic fraction is recovered as a supernatant. Provided that neither the cell membranes nor the nuclear membranes are dissolved, the cells are present as precipitates and RNA should not be extracted from the supernatant. By contrast, when both of these membranes are dissolved, the supernatant should produce the same results as those obtained by the complete dissolution of the cells.

Thus, from among the surfactants used in Example 1, Triton X-100, Brij 35, Brij 58, octyl-thioglucopyranoside (OTG), and CHAPS were selected and separately prepared into 0.025, 0.11, 0.01, 0.28, and 0.5% PBS solutions, to which $10^5$ K562 cells were in turn added. Table 2 shows the amounts of various solutions used in the experiment.

TABLE 2

| Each detergent | 1% stock solution | PBS | Cell ($10^5$/ml of PBS) |
|---|---|---|---|
| Triton X-100 | 5 μl | 95 μl | 100 μl |
| Brij35 | 22 | 78 | 100 |
| Brij58 | 2 | 98 | 100 |
| OTG | 56 | 44 | 100 |
| CHAPS | 100 | 0 | 100 |

Then, the solutions were centrifuged at 500 g for 3 minutes, and the supernatants were recovered. RNA was recovered from the supernatants using Qiagen RNeasy™ Mini Kit. Specifically, 200 μl of RLT solution included in the kit was added to 200 μl of each supernatant obtained by centrifugation. The RNA fraction was adsorbed onto a column by the addition of 350 μl of 70% ethanol. Then, the column was washed with a washing solution included therein according to the recommended protocol. Finally, RNA was eluted and recovered using 30 μl of RNase-free distilled water.

On the other hand, RNA was extracted as a control experiment using a general-purpose reagent kit for direct RNA extraction from cells without nuclear fractionation, and the

TABLE 1

Dilution ratios of various detergents and morphology of K562 cells treated at the concentrations

| Concentration | ×1 | | | ×0.1 | | | ×0.01 | | | ×0.001 | | | CMC (%) | Cloud Point (°C.) |
|---|---|---|---|---|---|---|---|---|---|---|---|---|---|---|
| | 7.5 | 5.0 | 2.5 | 7.5 | 5.0 | 2.5 | 7.5 | 5.0 | 2.5 | 7.5 | 5.0 | 2.5 | | |
| TritonX-100 | – | – | – | – | | | | + | + | + | + | + | 0.015 | 64 |
| TritonX-114 | | | | | | | | | | | | | 0.011 | 23 |
| NP 40 | – | – | – | | | | | | + | + | + | + | 0.018 | 80 |
| Tween 20 | | | | | | | + | + | + | + | + | + | 0.007 | >100 |
| Tween 80 | | | | | | | + | + | + | + | + | + | 0.002 | >100 |
| Brij 35 | | | | | | | | + | + | + | + | + | 0.11 | 95 |
| Brij 58 | – | – | – | | | | | + | + | + | + | + | 0.009 | – |
| OG | | | | | + | + | + | + | + | + | + | + | 0.67 | >100 |
| OTP | | | | | | + | + | + | + | + | + | + | 0.28 | >100 |
| CHAPS | | | | | | + | + | + | + | + | + | + | 0.47 | >100 |

OG: Octyl-Clucoside
OTP: Octyl-Thiopyranoside
+ Cells aggregated with each other and had different color in their centrol parts.
░ Cells were dispersed, and the outline of each cell was observed bit its central part was difficult to differentiate.
– The outline was also lost amount of RNA extracted was compared therewith. Specifically, RNA was extracted using RNeasy™ Mini Kit according to the protocol. The protocol involves: subjecting 100 µl of a cell suspension to centrifugation at 300 g for 5 minutes to recover cells, which are then homogenized by the addition of 350 µl of RLT solution; adsorbing the RNA fraction onto a column by the addition of 350 µl of 70% ethanol; and washing the column with a washing solution, followed by elution with distilled water.

Figure 4:
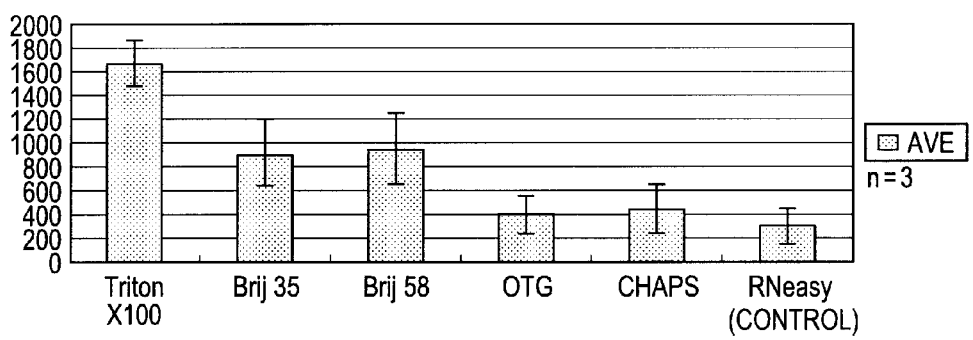
FIG. 4 illustrates the recovery (pg/μl) of RNA prepared by a conventional method or a method of the present invention.

The eluted RNA was analyzed using Agilent BioAnalyzer™ RNA 6000 Pico Kit. The results are illustrated in FIG. 4.

All the surfactants exhibited a higher recovery rate than that of RNA extraction from the whole cells. This can suggest that the nuclear fractionation can prevent large-scale contamination with macromolecules (i.e., DNA) contained in the nuclei, and as a result, RNA is recovered easily.

Example 3

Next, the replacement of filter treatment for the centrifugation performed in Example 2 was studied. After the surfactant treatment performed in Example 2, cells were (i) centrifuged in the same way as in Example 2 or (ii) homogenized through an injection needle and then passed through Millipore Millex LG (hydrophilic PTFE, pore size: 0.2 µm) to recover a pass-through fraction. Then, in the same way as in Example 2, the RNA fraction was adsorbed, by the addition of 200 µl of RLT solution and 350 µl of 70% ethanol, onto a column included in the kit, which was then washed with a solution included therein, followed by total RNA recovery. The same K562 cells as in Example 2 were used in this study at cell numbers of $10^5$ and $10^4$. The different numbers of the cells were used because the number of white blood cells varies by approximately 10 times in disease patients and further because the centrifugation of a small number of cells would easily lyse the cells due to their collision with the wall.

Figure 5A:
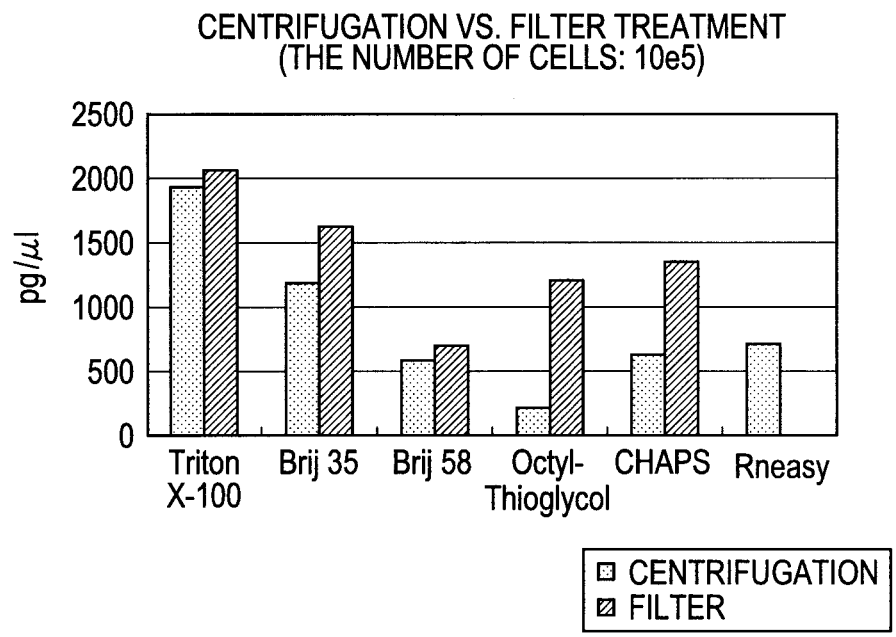
FIGS. 5A and 5B illustrate the recovery of RNA after nuclear separation performed by centrifugation or using a filter.
Figure 5B:
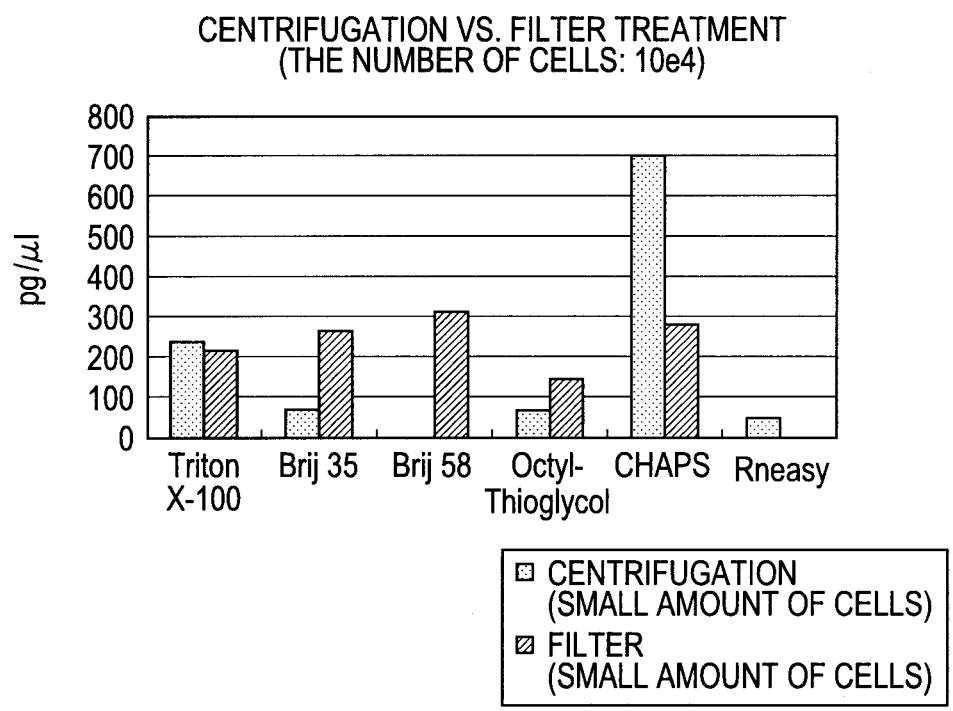

However, in this Example, the concentrations of all surfactants were adjusted to concentrations 2 times their CMCs (in Example 2, only Triton X-100 was used at a concentration 2 times its CMC, and the other surfactants were used at concentrations 1 time their CMC values). Table 3 shows the amounts of the solutions used. The results are illustrated in FIGS. 5A and 5B.

TABLE 3

| Each detergent | 1% stock solution | PBS | Cell ($10^6$/ml of PBS) |
|---|---|---|---|
| Triton X-100 | 6 µl | 94 µl | 100 µl |
| Brij35 | 44 | 56 | 100 |
| Brij58 | 4 | 96 | 100 |

As a result of evaluation using BioAnalyzer™ RNA 6000 Pico Kit, the recovery using the filter in all the cases exhibited a higher RNA recovery rate than that obtained by centrifugation. Even when the amount of nucleic acids was almost the same or larger for centrifugation, these recovered products were shown to not only contain RNA but also be contaminated with DNA (rRNA ratio and 28S/18S ratio). Particularly, the final products recovered by centrifugation from a small number of cells had an RNA content to an extent where somewhat RNA peaks were observed on the DNA background.

Figure 6B:
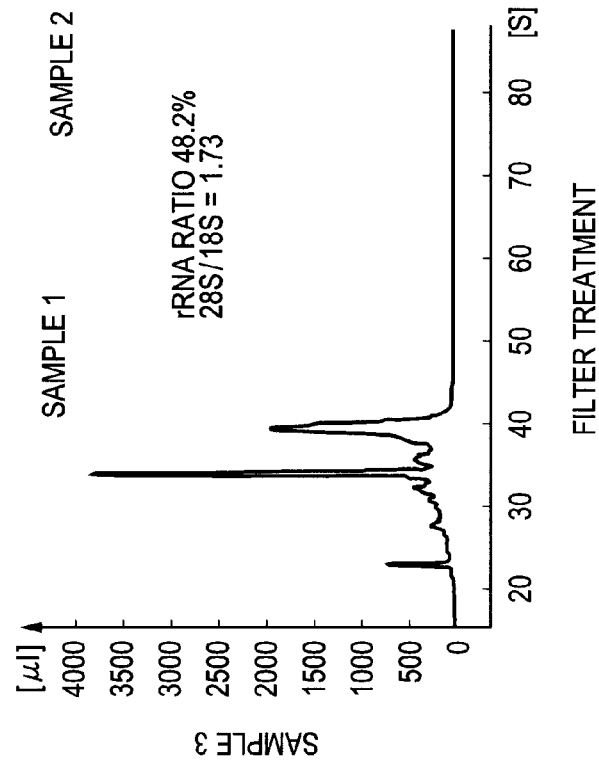
FIGS. 6A and 6B illustrate results of evaluating RNA prepared by a conventional method (centrifugation) and the method of the present invention and shows DNA contamination in the conventional method.
Figure 6A:
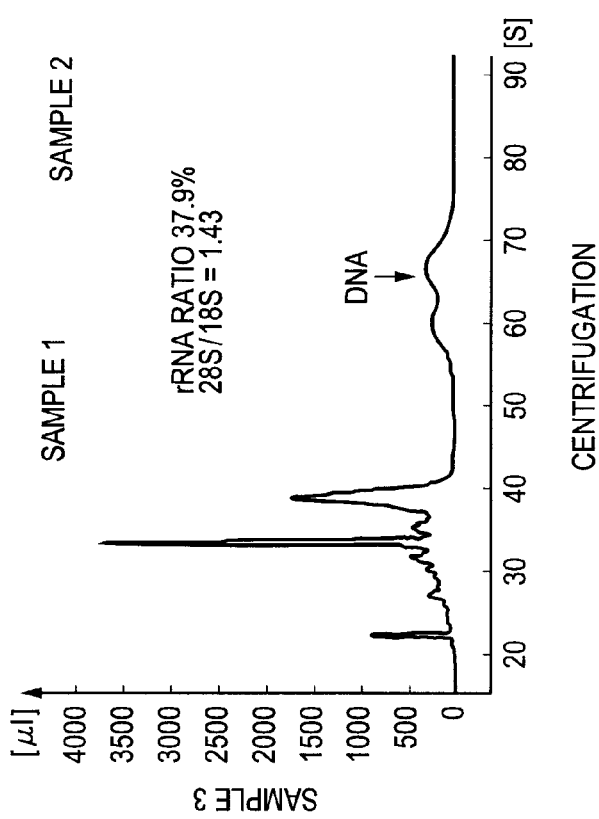

FIGS. 6A and 6B illustrates results of centrifugation (FIG. 6A) or filter treatment (FIG. 6B) after treatment with Triton X-100. The eluates at 33 seconds and around 40 seconds are 18S rRNA and 28S rRNA, respectively. Since longer nucleic acid components detected in the sample after centrifugation are deleted by DNase I treatment, these components can probably be relegated as DNA.

Example 4

RNA recovery was compared between another conventional method (free from nuclear fractionation) and the method of the present invention. The most general RNA extraction method involves: using guanidine thiocyanate to strongly denature all protein fractions containing even RNase in samples after cell lysis; and performing phenol/chloroform extraction after such inhibition of RNA decomposition. This method is regarded as being capable of extracting RNA most stably. This method was compared with the method of the present invention.

Ambion mirVana PARIS™ Kit elutes RNA through the procedures of: dissolving cells in a cell-lysing solution; then denaturing proteins with guanidine thiocyanate; then performing phenol/chloroform extraction; adsorbing the RNA fraction onto a glass fiber column by the addition of ethanol to the aqueous solution fraction; and washing the column in several stages.

Alternatively, Ambion PARIS™ Kit involves the same operation to the guanidine thiocyanate treatment as in the mirVana PARIS™ Kit and however elutes RNA through the phenol extraction-free procedures of adsorbing the RNA-containing fraction onto a glass fiber column by the addition of ethanol, followed by washing.

Figure 7:
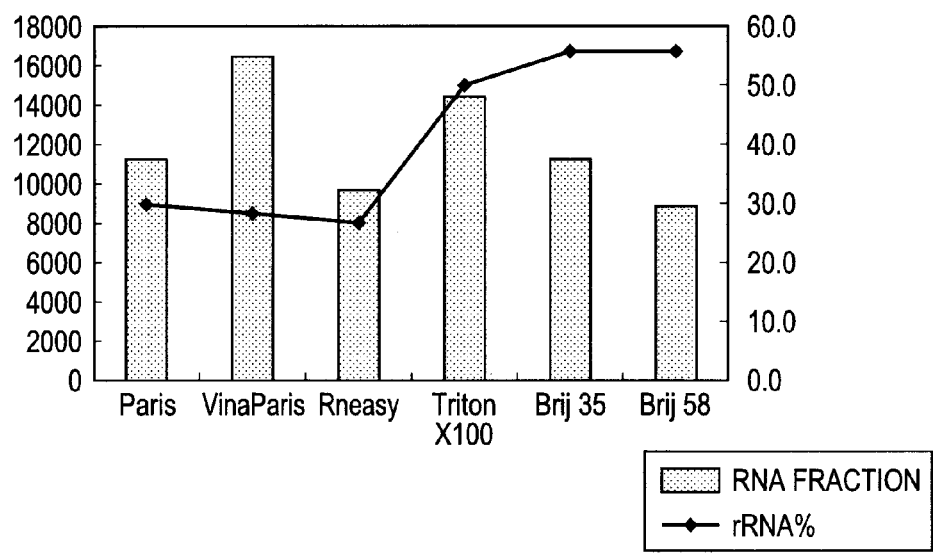
FIG. 7 illustrates the recovery (pg/μl) of an RNA fraction obtained by the conventional method or the method of the present invention and an rRNA content (%) in the obtained RNA fraction.

These kits were used to extract RNA from $10^5$ K562 cells according to the recommended protocol. Furthermore, according to the procedures described in Example 3, cells after treatment with Triton X-100, Brij 35, or Brij 58 were homogenized and then passed through a filter to obtain a pass-through fraction, from which an RNA fraction was then extracted by column adsorption. The recovery of the obtained RNA fraction, the content of rRNA (which corresponds to almost the total RNA amount) in the extracted RNA fraction, and a 28S/18S ratio (higher 28S/18S ratio indicates that more RNA is extracted without being decomposed) were compared between these methods. Of them, the results as to the recovery of the RNA fraction and the content of rRNA in the prepared nucleic acid fraction are illustrated in FIG. 7.

The results indicate that the method of the present invention dose not always achieve the maximum recovery of the RNA fraction and the extraction using the mirVana PARIS™ Kit offers a higher recovery. However, the RNA fraction obtained as an eluate using the mirVana PARIS™ Kit had a low rRNA content. Both the PARIS™ Kit and the mirVana PARIS™ Kit yielded an rRNA content of 30% or lower, whereas the RNA fraction extracted by the method of the present invention had an rRNA content as high as 50% or higher, demonstrating that the actual RNA content occupying the obtained RNA fraction is high.

Thus, the existing methods including extracting the desired fraction after lysis of the whole cells were found to have poor extraction efficiency and be inferior in the amount and quality of RNA in the extract. The method of the present invention including extracting RNA after nuclear fractionation by surfactant treatment and filter treatment was demonstrated to be superior thereto in terms of both the amount and the quality.

Example 5

Previously reported conditions of surfactant concentrations for nuclear and cytoplasmic separation are 0.3% NP40, 0.3% Triton X-100, and 1% Tween 20. Since their CMCs are 0.018% (NP40), 0.015% (Triton X-100), and 0.0074% (Tween 20), the previously reported conditions correspond to 17 times, 20 times, and 135 times their CMCs, respectively.

An experiment was conducted in the same way as in Example 3 at varying concentrations of surfactants for the purpose of determining a surfactant concentration range relative to the CMC effective for fractional dissolution in which nuclear membranes are preserved while cell membranes are dissolved. The experiment was conducted under conditions of the surfactant concentrations set to 1, 2, 5, 10, 20, and 30 times their CMCs.

Figure 8:
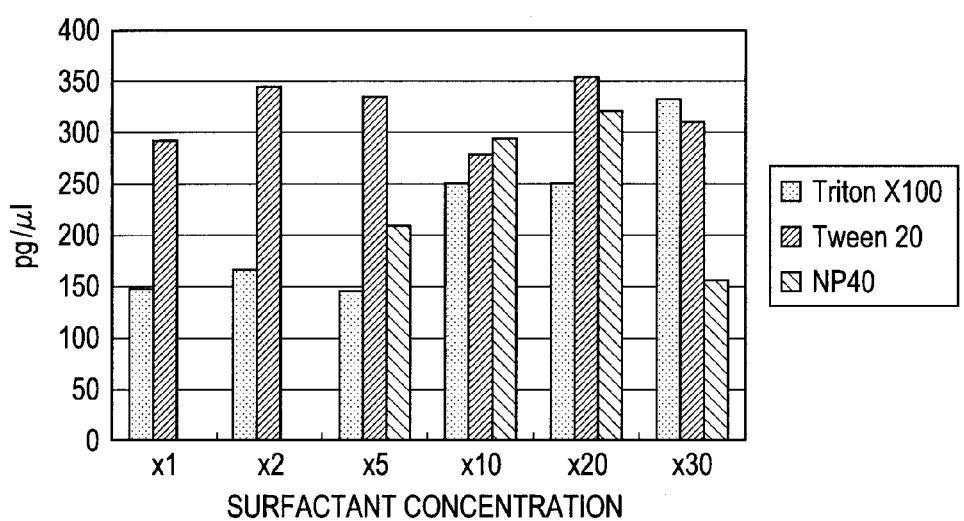
FIG. 8 illustrates magnifications of various surfactants relative to their CMCs and the amount of RNA extracted from cells treated at the concentrations.
Figure 9:
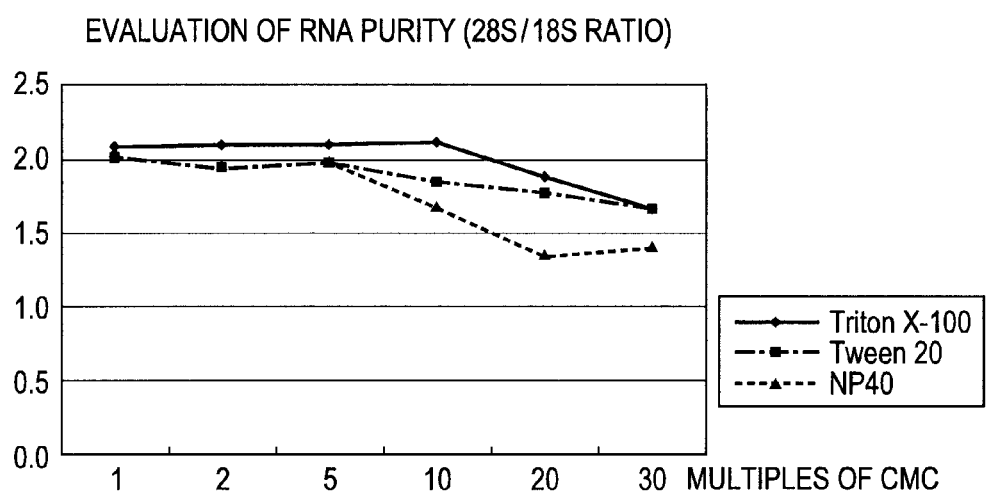
FIG. 9 illustrates a 28S rRNA/18S rRNA ratio that serves as an index for RNA integrity.

The experiment results are illustrated in FIGS. 8 and 9. FIG. 8 illustrates the recovery of RNA. FIG. 9 illustrates the quantitative ratio between 28S rRNA and 18S rRNA. Since 28S rRNA and 18S rRNA are 4800 bp and 1900 bp, respectively, in base length, the quantitative ratio between 28S rRNA and 18S rRNA is theoretically calculated as 2.5.

In fact, higher surfactant concentrations tend to improve extraction efficiency (Triton X-100 and NP40). However, the 18S/28S rRNA ratio is 2 or more up to a surfactant concentration 5 times the CMC, whereas this ratio is declined around a surfactant concentration 5 to 10 times the CMC, indicating increase in the amount of decomposition products. Based on these results, the optimum surfactant concentration is 1 to 10 times the CMC and can be equal to or lower than 5 times the CMC.

Example 6

In the same way as in Example 3, cells were treated with each of three surfactants Triton X-100, Brij 35, and Brij 58. Then, mRNA was extracted from a cytoplasmic lysate obtained as a filter-pass-through fraction. Specifically, mRNA was extracted using TAKARA Oligotex-dT30 super mRNA Purification Kit according to the recommended protocol. The successful mRNA extraction was confirmed by analysis using Agilent BioAnalyzer™.

Example 7

Cultured Cells; K562 cells were grown in RPMI 1640 containing 10% FBS, 500 units/ml penicillin, and 500 μg/ml streptomycin and subcultured twice a week at a ratio of approximately 1:10. The cells were recovered, then washed with a PBS solution, and then suspended at a concentration of $10^6$ cells/ml in a PBS solution. This cell suspension was injected at a cell number of $10^6$, $5 \times 10^5$, $10^5$, or $5 \times 10^4$ to a filter Millex SV manufactured by Millipore Corp. (filter diameter: 25 mm, pore size: 5 μm) to immobilize the cells onto the filter. Next, this filter was connected to a filter Millex HV manufactured by Millipore Corp. (filter diameter: 13 mm, pore size: 0.45 μm) such that the Millex HV filter was placed under the Millex SV filter. A PBS solution of a surfactant was pressure-injected in an amount of 400 μl from the inlet of the Millex SV using a syringe. The surfactant was 0.075% Triton X-100, 0.55% Brij 35, or 0.043% Brij 58. All of these concentrations correspond to 5 times the CMCs of the surfactants.

Approximately 400 μl of components that passed through the two filters was recovered. The RNA fraction was adsorbed, by the addition of 400 μl of RLT solution and 700 μl of 70% ethanol, onto a column included in RNeasy™ Mini Kit in the same way as in Example 2. Total RNA was recovered according to the protocol of the kit.

Figure 10:
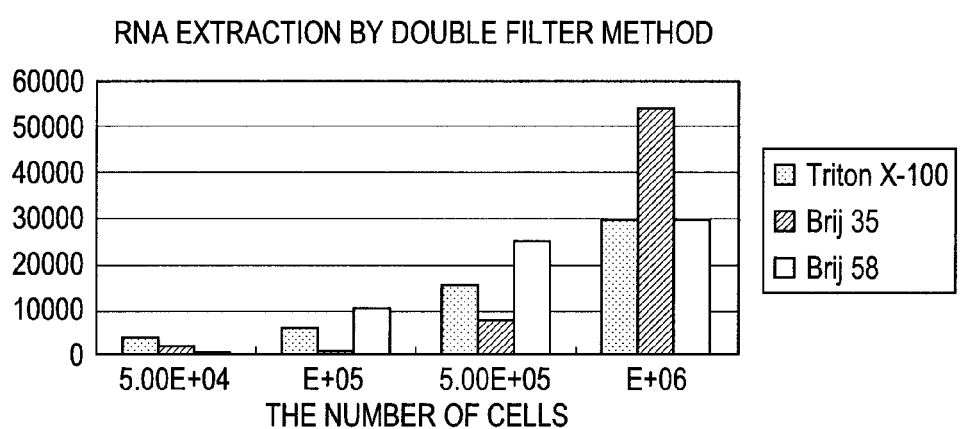
FIG. 10 illustrates the yield (pg/μl) of RNA obtained by a double filter method (Example 7)

The eluted total RNA was analyzed using Agilent BioAnalyzer™ RNA 6000 Pico Kit. The results are illustrated in FIG. 10.

Approximately 5000 pg/μl or higher RNA was obtained using Triton X-100, indicating that the homogenization using the double filter is effective.

Example 8 mRNA Extraction

From the RNA fraction obtained in Example 7, mRNA was extracted using Qiagen FastTrack™ MAG Micro mRNA Isolation Kit. Specifically, 170 μl of distilled water was added to 30 μl of the RNA extracted using RNeasy. mRNA was bound to oligo(dT) bound with MAG Beads by the addition of 200 μl of a binding buffer solution and 30 μl of the MAG Beads. The beads were washed with a washing buffer included therein. Then, mRNA was recovered using 30 μl of RNase-free water. From 4 μl of the extracted mRNA, cDNA was further synthesized using Invitrogen SuperScript™ First-Strand Synthesis SuperMix according to the protocol.

Figure 11:
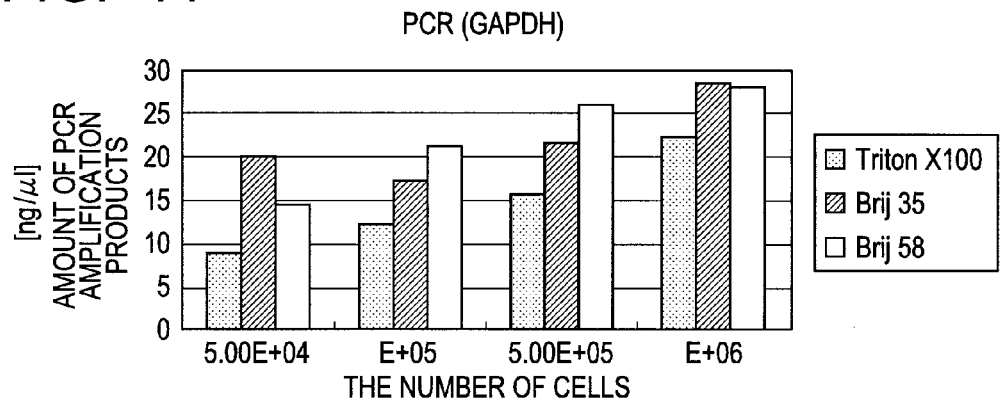
FIG. 11 illustrates the amount of PCR amplification products obtained as a result of Example 8.

Next, whether or not cDNA was synthesized was confirmed through PCR reaction using GAPDH and β-actin gene primers (QuantiTest Primer Assay manufactured by Qiagen GmbH). Forty PCR cycles each involving 95° C. for 5 seconds and 60° C. for 10 seconds were performed with 3 μl of cDNA from the Triton X-100-extracted product as a template. The amount of amplification products was evaluated using BioAnalyzer™. With increase in initial cell number ($5 \times 10^4$, $10^5$, $5 \times 10^5$, and $10^6$), the concentration of PCR amplification products (GAPDH) monotonically increased from 9 to 22 ng/μl. PCR amplification was also confirmed for Brij 35 and Brij 58 (the same level as in Triton X-100), demonstrating that mRNA was present in the RNA fraction extracted by the RNA extraction method using the double filter (FIG. 11).

Example 9

Figure 12:
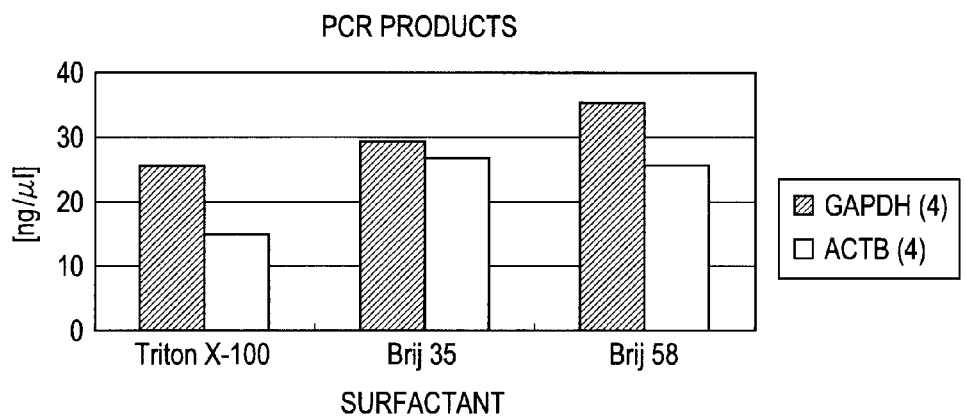
FIG. 12 illustrates the amount of PCR amplification products obtained as a result of Example 9.

Direct mRNA recovery from the eluted surfactant solution that passed through the double filter in Example 7 was attempted by adding 30 μl of FastTrack™ MAG beads to the eluted solution without extracting an RNA fraction therefrom. In the experiment, $10^6$ cells were used. The procedures are the same as in Example 8. Moreover, subsequent cDNA synthesis and PCR amplification reaction were also performed in the same way as in Example 8. The concentrations of PCR amplification products from the Triton X-100 solution were 14 ng/μl (β-actin) and 25 ng/μl (GAPDH). Brij 35 yielded concentrations of 26 and 29 ng/μl, respectively. Brij 58 yielded concentrations of 25 and 34 ng/μl, respectively. It was thus demonstrated that mRNA could be extracted at the same level as in Example 8 (FIG. 12).

Example 10 mRNA extraction was performed using blood. To 100 μl of peripheral blood (refrigerated), an equal amount of distilled water was added, and the mixed solution was injected to a filter Millex SV (filter diameter: 25 mm, pore size: 5 μm). Then, the filter was washed with 1 ml of PBS and connected to a filter Millex HV (filter diameter: 13 mm, pore size: 0.45 μm).

A PBS solution of a surfactant was pressure-injected in an amount of 500 μl from the inlet of the Millex SV using a syringe. The surfactant was 0.075% Triton X-100, 0.55% Brij 35, or 0.043% Brij 58. All of these concentrations correspond to 5 times the CMCs of the surfactants.

Figure 13:
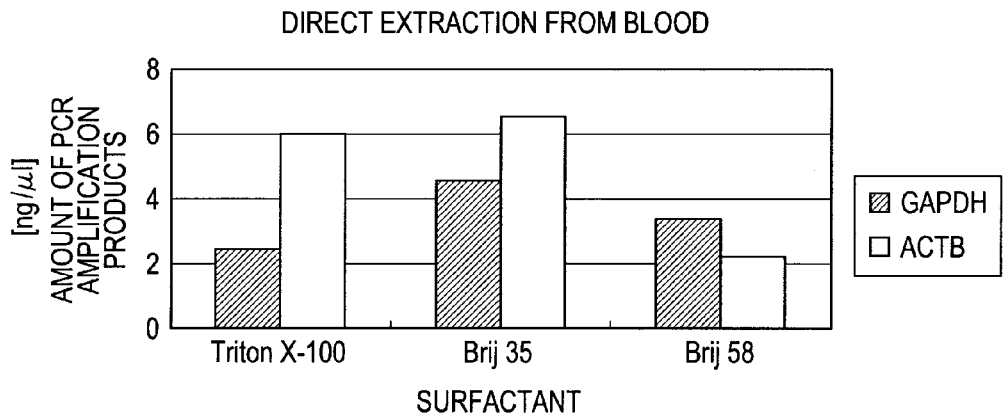
FIG. 13 illustrates the amount of PCR amplification products obtained as a result of Example 10.

To the eluted solution, 30 μl of FastTrack™ MAG beads was added, and 50 μl (1/10 volume) of a 3 M NaCl solution was further added thereto instead of a binding buffer solution. The mixture was heated at 70° C. for 5 minutes and then stirred at room temperature for 10 minutes to bind oligo(dT) on the beads to mRNA. The beads were washed with a washing solution included therein. Then, mRNA was recovered using RNase-free water. In the same way as in Example 8, cDNA was further synthesized, and GAPDH or β-actin gene amplification was confirmed through PCR reaction to confirm the presence of mRNA. The amounts of amplification products were 2 to 4 ng/μl (GAPDH) and 5 to 6 ng/μl (β-actin) for all the surfactants (FIG. 13).

This indicates that mRNA can be recovered by: passing hemolyzed blood through a filter (Millex SV); washing off components other than white blood cells using PBS; then connecting a filter for nuclear separation (Millex HV) thereto; pressure-injecting a surfactant at a concentration 5 times its CMC using a syringe from above the Millex SV; and adding oligo(dT)-bound magnetic beads to the surfactant solution that has passed therethrough.

Example 11

To the filter with the nuclear fraction captured thereon in Example 6, 200 μl of a 10 mM tris-HCl buffer solution (pH 8.0) containing 1% SDS and 1 mM EDTA and 10 μl of 20 mg/ml proteinase K was added. The nuclear fraction on the filter was recovered by pushing out air in the direction opposite to the usual direction using an air-filled syringe barrel. This fraction was reacted at 37° C. for 60 minutes and then mixed with sodium iodide added at a final concentration of 4.5 M and then with 0.5 ml isopropanol added. After centrifugation at 12000 rpm for 10 minutes, DNA was recovered as precipitates. The obtained DNA was washed with 40% isopropanol, then dried, and then dissolved in a TE buffer solution (10 mM tris-HCl buffer solution (pH 8.0) containing 1 mM EDTA) to obtain DNA.

Example 12

To 1 ml of peripheral blood, 1 ml of RNase-free distilled water was added. In the same way as in Example 10, the mixed solution was passed through Millex SV to capture white blood cells on the filter. Then, the filter was washed with 5 ml of PBS. In the same way as in Example 10, Millex HV was connected to the Millex SV. Triton X-100 at a concentration of 0.075% corresponding to a concentration 5 times its CMC was pressure-injected using a syringe from above the Millex SV.

A series of 2-fold dilution of the extract was prepared, then injected at a concentration of 100 μl/well to a microtiter plate, and fixed overnight at 4° C. The plate was washed twice with PBS containing 0.05% Tween 20 and reacted at room temperature for 2 hours with a solution of 1/100 diluted mouse GAPDH antibodies (manufactured by LFR) as primary antibodies. Again, the plate was washed twice with PBS containing 0.05% Tween 20 and then reacted with horseradish peroxidase-conjugated goat anti-mouse IgG as secondary antibodies. Then, proteins were quantified based on the degree of color development according to a standard method.

Significant color development was observed from the series of 1/8 to 1/64 dilutions, demonstrating that protein detection through antigen-antibody reaction could be achieved.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-132911, filed Jun. 2, 2009, which is hereby incorporated by reference herein in its entirety.

The invention claimed is:

1. A method for preparing, from one cell, each of a protein, DNA, and RNA, comprising performing nuclear and cytoplasmic separation by: treating the cell with a surfactant solution that lyses cell membranes but does not lyse nuclear membranes; homogenizing the treated cell solution by passing the treated cell solution thus obtained through a first filter which is a channel having a pore size that is impenetrable to cells but allows nuclei to pass therethrough; and further passing the treated cell solution thus obtained through a second filter comprising a membrane having such a pore size as to be impenetrable to nuclei but allow cytoplasmic ribosomes to pass therethrough; and then extracting each of a protein, DNA, and RNA, wherein the second filter is connected to the first filter such that the second filter is placed subsequent to the first filter, and wherein the second filter has a smaller area than the first filter.

2. The preparation method according to claim 1, wherein the surfactant is a nonionic surfactant and has a concentration not lower than its CMC (critical micelle concentration) and within 10 times its CMC (critical micelle concentration), and wherein the CMC (critical micelle concentration) refers to the minimal concentration of the surfactant necessary for forming a micelle of the surfactant.

3. The preparation method according to claim 1, wherein the pore size of the membrane is 0.2 to 5.0 μm.

4. The preparation method according to claim 3, wherein the pore size of the membrane is 0.2 to 1 μm.

5. The preparation method according to claim 1, wherein the pore size of the channel is 1.0 to 8.0 μm.

6. The preparation method according to claim 1, wherein the pore size of the channel is 1.0 to 5.0 μm.

7. The preparation method according to claim 1, comprising:
using the first filter to capture a cell on the first filter;
injecting the surfactant solution onto the first filter to cause reaction with the cell captured on the first filter;
and
passing a liquid through the first filter and the second filter by pressure injection to homogenize the treated cell solution, and to capture the nucleus on the second filter while passing a cytoplasmic fraction therethrough.

8. The preparation method according to claim 7, wherein the cell preparation method further comprises recovering mRNA through the reaction of the cytoplasmic fraction that has passed through the two filters with an oligo(dT)-bound support.

9. The preparation method according to claim 7, wherein the cytoplasmic fraction that has passed through the two filters is used in protein analysis.

10. The preparation method according to claim 1, wherein the area ratio between the second filter and the first filter is 50% or lower.

11. A method for preparing, from one cell, each of a protein, DNA, and RNA, comprising performing nuclear and cytoplasmic separation by:
   treating the cell with a surfactant solution that lyses cell membranes but does not lyse nuclear membranes; homogenizing the treated cell solution by passing the treated cell solution thus obtained through a first filter by pressure injection, the first filter being a channel having a pore size that is impenetrable to cells but allows nuclei to pass therethrough; and further passing the treated cell solution thus obtained through a second filter by pressure injection, the second filter comprising a membrane having such a pore size as to be impenetrable to nuclei but allow cytoplasmic ribosomes to pass therethrough; and then extracting each of a protein, DNA, and RNA, wherein the surfactant is a nonionic surfactant and has a concentration 1 to 5 times its CMC (critical micelle concentration), and wherein the CMC (critical micelle concentration) refers to the minimal concentration of the surfactant necessary for forming a micelle of the surfactant wherein the second filter is connected to the first filter such that the second filter is placed subsequent to the first filter, and wherein the second filter has a smaller area than the first filter.

12. The preparation method according to claim 11, wherein the area ratio between the second filter and the first filter is 50% or lower.

* * * * *